(12) United States Patent
Yuan et al.

(10) Patent No.: US 11,328,338 B1
(45) Date of Patent: May 10, 2022

(54) RECOMMENDATION MATRIX

(71) Applicant: Life Spectacular, Inc., San Francisco, CA (US)

(72) Inventors: Zaoshi Amy Yuan, San Francisco, CA (US); Ming S. Zhao, San Francisco, CA (US)

(73) Assignee: Life Spectacular, Inc., San Francisco, CA (US)

( * ) Notice: Subject to any disclaimer, the term of this patent is extended or adjusted under 35 U.S.C. 154(b) by 0 days.

(21) Appl. No.: 17/014,161

(22) Filed: Sep. 8, 2020

Related U.S. Application Data

(60) Provisional application No. 62/899,433, filed on Sep. 12, 2019.

(51) Int. Cl.
*G16H 10/60* (2018.01)
*G06Q 30/06* (2012.01)
*A61B 5/00* (2006.01)
*G16H 50/30* (2018.01)
*G16H 50/20* (2018.01)

(52) U.S. Cl.
CPC ......... *G06Q 30/0631* (2013.01); *A61B 5/441* (2013.01); *A61B 5/486* (2013.01); *G16H 10/60* (2018.01); *G16H 50/30* (2018.01); *G16H 50/20* (2018.01)

(58) Field of Classification Search
CPC .... G06Q 30/0631; G16H 10/60; G16H 50/30; G16H 50/20; A61B 5/441; A61B 5/486

USPC .................................................. 705/2–3, 26.7
See application file for complete search history.

(56) References Cited

U.S. PATENT DOCUMENTS

| | | | |
|---|---|---|---|
| 10,546,658 B2* | 1/2020 | Salvi | A45D 44/00 |
| 2004/0202685 A1* | 10/2004 | Manzo | A45D 44/00 424/401 |
| 2006/0229912 A1* | 10/2006 | Negishi | G16H 10/20 705/2 |
| 2006/0265244 A1* | 11/2006 | Baumann | A61B 5/441 705/2 |
| 2008/0126129 A1* | 5/2008 | Manzo | C23C 14/0005 705/2 |
| 2016/0331308 A1* | 11/2016 | Zhou | A61B 5/0022 |
| 2018/0374140 A1* | 12/2018 | Stucki | G06F 3/0482 |
| 2019/0237194 A1* | 8/2019 | Salvi | G16H 10/60 |
| 2019/0347296 A1* | 11/2019 | Parkkinen | G06Q 30/0201 |

* cited by examiner

*Primary Examiner* — Michael Tomaszewski
(74) *Attorney, Agent, or Firm* — Brownstein Hyatt Farber Schreck, LLP

(57) ABSTRACT

A method of providing a skincare regimen recommendation and curated skincare product portfolio is described. A user may enter user skincare data and a user skin profile may be generated from this data. The user skin profile may be mapped to skin matrix factors of a user skin profile matrix to derive a skin profile identifier. The skin profile identifier may be used to select ingredients to formulate a curated product line, specific to the skin issues that the user identified. A recommendation for the curated product line may be provided to the user as well as the option for the user to purchase an individual curated product or the entire product line.

17 Claims, 9 Drawing Sheets

600

| | MATRIX FACTOR X1 | MATRIX FACTOR X2 | MATRIX FACTOR X3 | MATRIX FACTOR X4 |
|---|---|---|---|---|
| MATRIX FACTOR Y1 | A11 | | | |
| MATRIX FACTOR Y2 | | B22 | | |
| MATRIX FACTOR Y3 | | | | D43 |
| MATRIX FACTOR Y4 | | | | |
| MATRIX FACTOR Y5 | | | C35 | |
| | | | | |
| | | | | |
| | | | | |
| | | | | |

*FIG. 6*

RECOMMENDATION MATRIX

CROSS-REFERENCE TO RELATED APPLICATION

This application is a nonprovisional of and claims the benefit under 35 U.S.C. 119(e) of U.S. Provisional Patent Application No. 62/899,433, filed Sep. 12, 2019, the contents of which are incorporated herein by reference as if fully disclosed herein.

FIELD

Embodiments described herein relate generally to a method of providing a skincare regimen recommendation and curated skincare product portfolio to a user, and more specifically to using a skin profile matrix to select curated products for a user.

BACKGROUND

Skincare products are used by men, women, and children every day. These skincare products are available for purchase, for example in various department stores, grocery stores, beauty specialty stores, and websites. In all of these settings, the skincare products are sitting on shelves and ready for purchase. Although there are various skincare product lines to address the skincare needs of individuals, unless the individual fits within one of the broad skincare categories of the product lines, there may be no product that addresses the individual's skin care issues.

Additionally, the users of the skincare products may have widely varying skin types. Although, the varying skin types may differ in a number of ways including the oil production by the skin and other factors such as sun exposure, users may select the same skincare product off the shelf of a department store. In some cases, the same skincare product may not exacerbate the existing skincare issues of the users, but in many cases the product may be more effective for one person than the other. Selecting skincare products may present drawbacks to the user as buying off the shelf products may not address the prioritized skincare needs of the user. Further, the product line may not address the user's individualized skincare issues.

SUMMARY

Embodiments of the methods described in the present disclosure are directed to a method for providing a custom curated skincare product line to a user. Also described are methods directed to recommending and providing a curated skincare product recommendation to a user that addresses the specific needs and issues of the user. A user skin profile may be generated and mapped onto a user skin profile matrix. A skin profile identifier may be derived from this mapping and the skin profile identifier may be used to create a curated set of skincare products that specifically address the individual and specific needs and circumstances of the user.

In some examples, the present disclosure describes a method of providing a skincare regimen recommendation based at least in part on a user skin profile. The method may include creating a user skin profile matrix using a set of skin matrix factors, deriving a skin profile identifier from the user skin profile matrix, using the skin profile identifier to create a curated set of skincare products, and providing the curated set of skincare products to a user. The method may also include adapting the skin profile identifier according to an anticipated change to the user skin profile to create an updated curated set of skincare products for the user and receiving user data for use in generating the user skin profile. In some examples, deriving the skin profile identifier from the user skin profile matrix may include mapping the user skin profile to the user skin profile matrix and may also include concatenating individual representative markers of each of the skin matrix factors mapped to the user skin profile.

In some examples, the method may include generating the user skin profile, wherein the user skin profile comprises at least one of seasonal variations or environmental conditions and selecting the set of skin matrix factors to represent the user skin profile, wherein the set of skin matrix factors comprises at least one of skin information or user information. In further examples, the method may include assigning an individual representative marker to each of the skin matrix factors of the set of skin matrix factors, of the user skin profile matrix. In still further examples, the method may include scheduling automatic updates to the curated set of skincare products for the user based at least in part on the user skin profile. In additional examples, the method may include creating the updated curated set of skincare products for the user based at least in part on when the automatic update signals an anticipated change to the user skin profile and providing the updated curated set of skincare products to the user.

In some examples, the present disclosure describes a method directed to dynamically providing a skincare product recommendation which may include recommending an individually curated set of skincare products to a user based at least in part on an initial user skin profile and using an initial skin profile identifier, generating an updated user skin profile and an updated skin profile identifier, where the updated user skin profile is based at least in part on an anticipated update included in the initial user skin profile, and recommending an updated individually curated set of skincare products to the user, where the updated user skin profile and the initial user skin profile are different. In some examples, generating the updated skin profile identifier may include triggering an anticipated update to the initial user skin profile and/or may include revising the initial user skin profile with an anticipated change that affects the inclusion of at least one of a base ingredient or an additive of the individually curated set of skincare products for the user.

In some examples, the method may include any or all of generating the initial skin profile identifier by correlating the initial user skin profile to a user skin profile matrix, creating the user skin profile matrix by selecting a set of skin matrix factors that include at least one of a set of skin factors or a set of non-skin factors, and formulating the individually curated set of skincare products for the user by selecting at least one base ingredient from a set of base ingredients or by selecting at least one additive from a set of additives, based at least in part on the initial skin profile identifier. In some examples, the method may include formulating the updated individually curated set of skincare products for the user by changing at least one ingredient from a set of base ingredients or by changing at least one additive from a set of additives and basing the change of ingredients at least in part on the updated skin profile identifier.

In some examples, the present disclosure describes a method of directed to creating a skincare regimen for a user, which may include selecting a set of skin matrix factors that includes at least one of a user skin descriptor or user information, constructing a user skin profile matrix that includes the set of skin matrix factors, deriving a skin profile identifier from the user skin profile matrix by mapping individual elements of a user skin profile to the skin matrix factors of the user skin profile matrix, and providing a customized skincare product line to a user, where the customized skincare product line is specifically matched to the user skin profile via the user skin profile matrix. In some examples, the method may include adapting the customized skincare product line for the user when a change to the user skin profile occurs and/or may include formulating the customized skincare product line for the user by curating at least one of a base ingredient of a set of ingredients or an additive of a set of additives.

In addition to the exemplary aspects and embodiments described above, further aspects and embodiments will become apparent by reference to the drawings and by study of the following description.

BRIEF DESCRIPTION OF THE DRAWINGS

The disclosure will be readily understood by the following detailed description in conjunction with the accompanying drawings, wherein like reference numerals designate like structural elements, and in which:

FIG. 6 illustrates an example skincare matrix;

Figure 1:
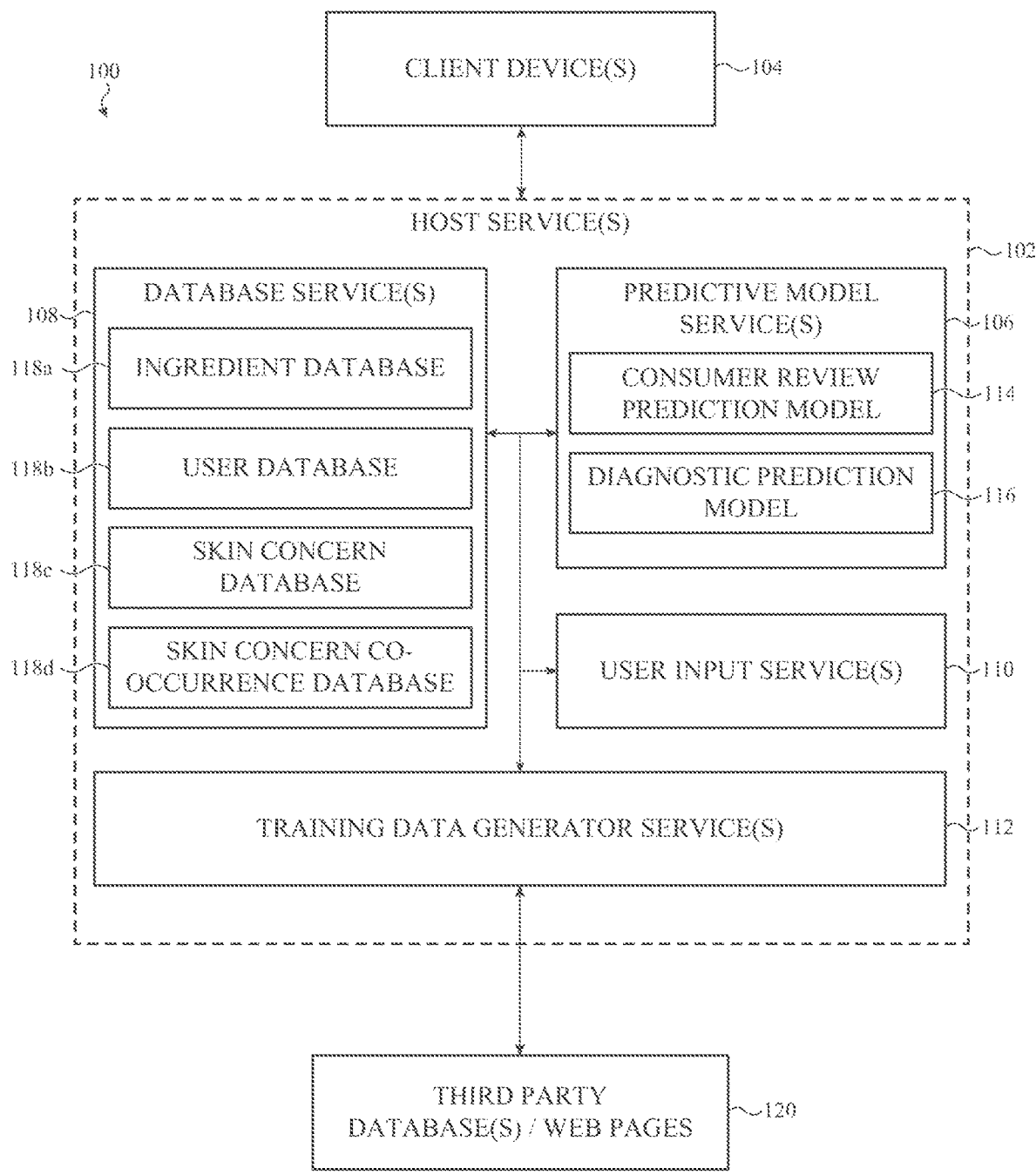
FIG. 1 illustrates an example recommendation engine of a skincare system.

It should be understood that the proportions and dimensions (either relative or absolute) of the various features and elements (and collections and groupings thereof) and the boundaries, separations, and positional relationships presented between them, are provided in the accompanying figures merely to facilitate an understanding of the various embodiments described herein and, accordingly, may not necessarily be presented or illustrated to scale, and are not intended to indicate any preference or requirement for an illustrated embodiment to the exclusion of embodiments described with reference thereto.

DETAILED DESCRIPTION

Reference will now be made in detail to representative embodiments illustrated in the accompanying drawings. It should be understood that the following description is not intended to limit the embodiments to one preferred embodiment. To the contrary, it is intended to cover alternatives, modifications, and equivalents as can be included within the spirit and scope of the described embodiments as defined by the appended claims.

Generally, in today's marketplace, users may select a skincare product or product line based on any number of factors, including: individual skin issues; allergies; articles in magazines; online reviews; the scent of the product; the product cost; marketing materials; the look of the product packaging; any combination thereof; and so forth. Recommendations may also be provided to the user by family and friends or in some cases by professional sales associates working for a retail store.

Users of skincare products may have widely varying knowledge bases regarding the types of skincare products that may be appropriate for the skin of the particular user. For example, the skin of a 15 year-old female user may be significantly different than the skin of a 36 year-old female. The two skin types may vary in a number of ways, including the oil production by the skin and other factors such as sun exposure, yet these two users may select the same skincare product off the shelf of a department store. Further, even though the 36 year-old female may be more aware of her skincare needs than the 15 year-old female, and even though they may base their skincare product selections on completely different criteria, they still may end up selecting the same skincare product due to the limited nature of currently available skincare products available for purchase. Although the same skincare product may work for the 15 year-old female and the 36 year-old female, in many cases the product may be more effective for one person than the other.

Further, the sellers of the skincare products or other self-styled "experts" may have a varying knowledge base of the different product lines, what the different products are used for and may have little knowledge regarding the intricacies of a user's skincare. As a result, skincare "experts" may recommend a product that is completely wrong for the user due to a general lack of knowledge of the product or the user. These recommendations may present drawbacks to the user such as paying for a product with no visible results, worsening skin conditions, and undesired skin reactions, among others.

The following disclosure generally relates to systems, process flows, and methods for recommending and providing a personalized skincare product or product line to a user, where the personalized skincare product line is specifically formulated for the user based on user information. User information may include skin related factors and non-skin related factors. The skin related factors may include information regarding oil production of the user's skin, allergies to ingredients, specific skin issues such as rosacea, acne, eczema, hyperpigmentation, fine lines, dark circles under the eyes, premature wrinkles, puffy eyes, crepey skin, or any combination thereof, and so forth. Non-skin related factors may include information regarding the geographic region in which the user resides, water intake, activity level, sun exposure, pollution levels, water hardness, or any combination thereof, and so forth. Skin related factors and non-skin related factors will be discussed in further detail herein.

The disclosure relates to systems, process flows, and methods for providing a curated skincare regimen recommendation for a user, based at least partially on a user skin profile. More specifically, the disclosure relates to employing a user skin profile matrix and a corresponding skin profile identifier to select curated products for a user. The user skin profile matrix may be one way of documenting a user's skin profile. The user skin profile matrix may be a multidimensional matrix, in that different data points of the user's skin profile may indicate an intersection or correlation of two, three, or more skincare factors. For example, a user's skin profile may include the correlated or intersecting skincare factors of being 19 years old, having oily skin, and living in a high humidity climate. Although each of these factors may be accounted for individually in multiple skincare products, when the intersecting skincare factors are simultaneously accounted for, a more effective skincare recommendation and product or product line may be provided to the user. Further, the user skin profile matrix and correspondingly, the skin profile identifier may be used to identify which ingredients which may best address the intersecting skincare factors of the user. In some examples, the ingredients may be categorized into base ingredients and additive ingredients. The base ingredients may be referred to herein as foundation ingredients and the additive ingredients may be referred to herein as additives or "boosters".

As one non-limiting example, individual user data may be received and a user skin profile may be generated from this user data. The individual user data may include information received from the user, who may be responding to a dynamic survey or questionnaire. In some examples, the dynamic questionnaire may ask questions in an order and with content specific to the user answering those questions. The dynamic questionnaire may be configured to present follow-up questions, to omit irrelevant questions (as determined by user input, user demographics, and/or answers to previously-presented questions), to ask supplemental questions, and so on. In some examples, the questions may be directed to skin conditions such as rosacea or eczema, skin issues such as dark spots or wrinkles, skin concerns such as aspects of their skin with which the user may be concerned, skin type such as oily, dry, combination, and so forth. Even though an aspect of the user's skin such as dark spots may be categorized as a skin issue, it may also fall into other categories such as a skin condition and a skin concern.

The user skin profile may be an entry in a client or customer database, which may be stored on, for example, a host server. The user skin profile may be further documented in a user skin profile matrix which may include a set of skin matrix factors. The skin matrix factors may include skin related factors and non-skin related factors which may affect the skin of an individual. The user skin profile may be mapped to the relevant skin matrix factors to produce the user skin profile matrix. A skin profile identifier may then be derived from the user skin profile matrix. The skin profile identifier may be a string of characters which may be representative of skin issues, conditions, and concerns of the user, along with any other relevant data such as seasonal changes, altitude, water alkalinity which may affect the user's skin.

Using this skin profile identifier, an individualized curated skincare product line may be created and/or selected for the user from a set of base ingredients and a set of additives. The curated skincare product line may be recommended to the user and provided to the user for purchase. In some examples, the skincare product line may include one or more of a facial cleanser; a topical sunscreen; a topical serum; an exfoliator; a moisturizer; a chemical peel; a toner; an eye cream; a night cream; or any combination thereof, and so forth.

Selecting a curated skincare product line according to the specific needs and issues of a user provides beneficial advantages to the user. For example, the curated skincare product line may be adaptable according to the user skin profile. In some examples, the user skin profile may include information regarding seasonal changes which correspond to where the user resides. The curated skincare product line may include different ingredients and may be adapted to the specific weather conditions of the user's geographic region. Some users may live in the southern part of the United States by the coast with high humidity and warm weather and other users may live in a landlocked state with very low humidity and a wide range of weather from below freezing to high altitude sun exposure. The ingredients of the curated skincare product line may change or be updated according to the temperature variations, the humidity variations, and the general sun exposure of the user. By changing the ingredients of the curated skincare product line, the products may address, mitigate and/or prevent specific issues that a user may experience.

These and other embodiments are discussed below with reference to FIGS. 1-9. However, those skilled in the art will readily appreciate that the detailed description given herein with respect to these figures is for explanatory purposes only and should not be construed as limiting.

FIG. 1 is an example recommendation engine, such as described herein. In the illustrated embodiment, the recommendation engine 100 is implemented with a client-server architecture including a host server 102 that communicably couples (e.g., via one or more networking or wired or wireless communication protocols) to one or more client devices, one of which is shown as the client device 104. The client device 104 and the host server 102 of the recommendation engine 100 can be configured to transaction information, such as, but not limited to: user demographic data; user geographic data; and so on.

It may be appreciated that other client devices may be configured in a substantially similar manner as the client device 104, although this may not be required of all embodiments and different client devices can be configured differently and/or may transact data or information with, and/or provide input(s) to, the host server 102 in a unique or device-specific manner.

The client device 104 can be any suitable personal or commercial electronic device and may include, without limitation or express requirement, a processor, volatile or non-volatile memory, and a display. Example electronic devices include, but are not limited to: laptop computers; desktop computers; wearable devices; cellular phones; tablet computing devices; and so on. It may be appreciated that a client device 104, such as described herein, can be implemented in any suitable manner.

In many embodiments, the processor of the client device 104 can be configured to execute an application (herein referred to as a "client application") stored, at least in part, in memory. The client application is configured to access and communicate with the host server 102 and to securely transact information or data with, and provide input(s) to, the host server 102. In some embodiments, the client application may be a browser application configured to access a web page or service hosted by the host server 102 that is accessible to the client device 104 over a private or public network that may, in some embodiments, include the open internet.

In many embodiments, the host server 102 is configured to operate within or as a virtual computing environment that is supported by one or more physical servers including one or more hardware resources such as, but not limited to (or requiring) one or more of: a processor; a memory; non-volatile storage; networking connections; and the like. For simplicity of description and illustration, these example hardware resources are not shown in FIG. 1.

In many embodiments, the host server 102 can include a number of discrete subservices or purpose-configured modules, containers, or virtual machines each configured to perform, coordinate, serve, or otherwise provide one or more services, functions, or operations of the host server 102, such as (1) serving a questionnaire to a user/user operating the client device 104, (2) receiving a response from the client device 104 containing user data (e.g., geographic data, questionnaire responses, demographic data, preference data and so on), (3) determining a diagnosis of one or more skin concerns presented by the user by leveraging a predictive model trained by information obtained from at least customer review data scraped from a public resource, (4) determining a user-specific ingredient list by leveraging a predictive model service 106 trained by information obtained from at least customer review data scraped from a public resource, and (5) determining or selecting a skincare product base and one or more skincare product additives that can be mixed together to create a user-specific skincare product. In addition, the host server 102 can be configured to generate training data (e.g., via a training data generator service 112) and to train the one or more predictive models.

To perform these and other operations, the host server 102 of the recommendation engine 100 can include one or more purpose-configured modules or services. For example, in many embodiments, the host server 102 includes a predictive model service 106, a database service 108, and a user input service 110, which may be communicably coupled to each other and/or to one or more other services or functional elements of the host server 102 (not shown).

The predictive model service 106 of the host server 102 can be configured to host and/or otherwise service requests to access one or more predictive models that may be trained in a particular manner and/or may serve a particular function. In other cases, the predictive model service 106 may also be configured to provide access to a consumer review predictive model 112 and/or a diagnostic prediction model 114 configured to ingest a diagnostic matrix, a user dataset and/or other information, and to output a customer review prediction matrix, entries of which correspond to a probabilistic assessment of likelihood that a particular ingredient, if used by the user in a recommended manner, would elicit a positive product review from that user. In still further embodiments, the predictive model service 106 can be configured to provide access to other predictive models, trained in any suitable manner. In many cases, a predictive model served by the predictive model service 106 of the host server 102 can be stored in any suitable form or format in a database accessible to the predictive model service 102. The predictive model service 106 and the various functions and operations thereof are described in greater detail with reference to embodiments that follow.

The database service 108 of the host server 102 can be configured to host and/or otherwise service requests to access to one or more databases or data sources, internal or external to the host server 102. Example databases, access to which is facilitated and/or controlled by the database server 108 are illustrated as the databases 118a-118d and can include, without limitation: an ingredient interaction database; a drug interaction database; an ingredient database; a product database; a customer review database; a scientific journal or study information database; and so on. In many cases, the database service 108 of the host server 102 can be configured to access one or more remote or third party databases 120 to obtain information. An example of a third party database that may be accessed by a database service, such as described herein, includes: a water hardness database; a weather prediction database; a customer database; a customer review database; a scientific journal or study database; and the like. The database service 108 and the various functions and operations thereof are described in greater detail with reference to embodiments that follow.

Each of the predictive model service 106 and the database service 108 are associated with allocations of physical or virtual resources, such as one or more processors, memory, and/or communication modules (e.g., network connections and the like), that such an implementation is not required. More generally, it may be appreciated that the various functions described herein of a host server 102 can be performed by any suitable physical hardware, virtual machine, containerized machine, or any combination thereof. Similarly, it may be appreciated that the client device 104 can be implemented in a number of suitable ways. In one embodiment, the client device 104 includes a processor, a memory, a display, and an input sensor or input device. These components can cooperate to perform or coordinate one or more operations of the client device 104 as it communicates with and transacts information with the host server 102.

The foregoing embodiment depicted in FIG. 1 and the various alternatives thereof and variations thereto are presented, generally, for purposes of explanation, and to facilitate an understanding of various configurations and constructions of a system, such as described herein. However, it will be apparent to one skilled in the art that some of the specific details presented herein may not be required in order to practice a particular described embodiment, or an equivalent thereof.

Figure 2:
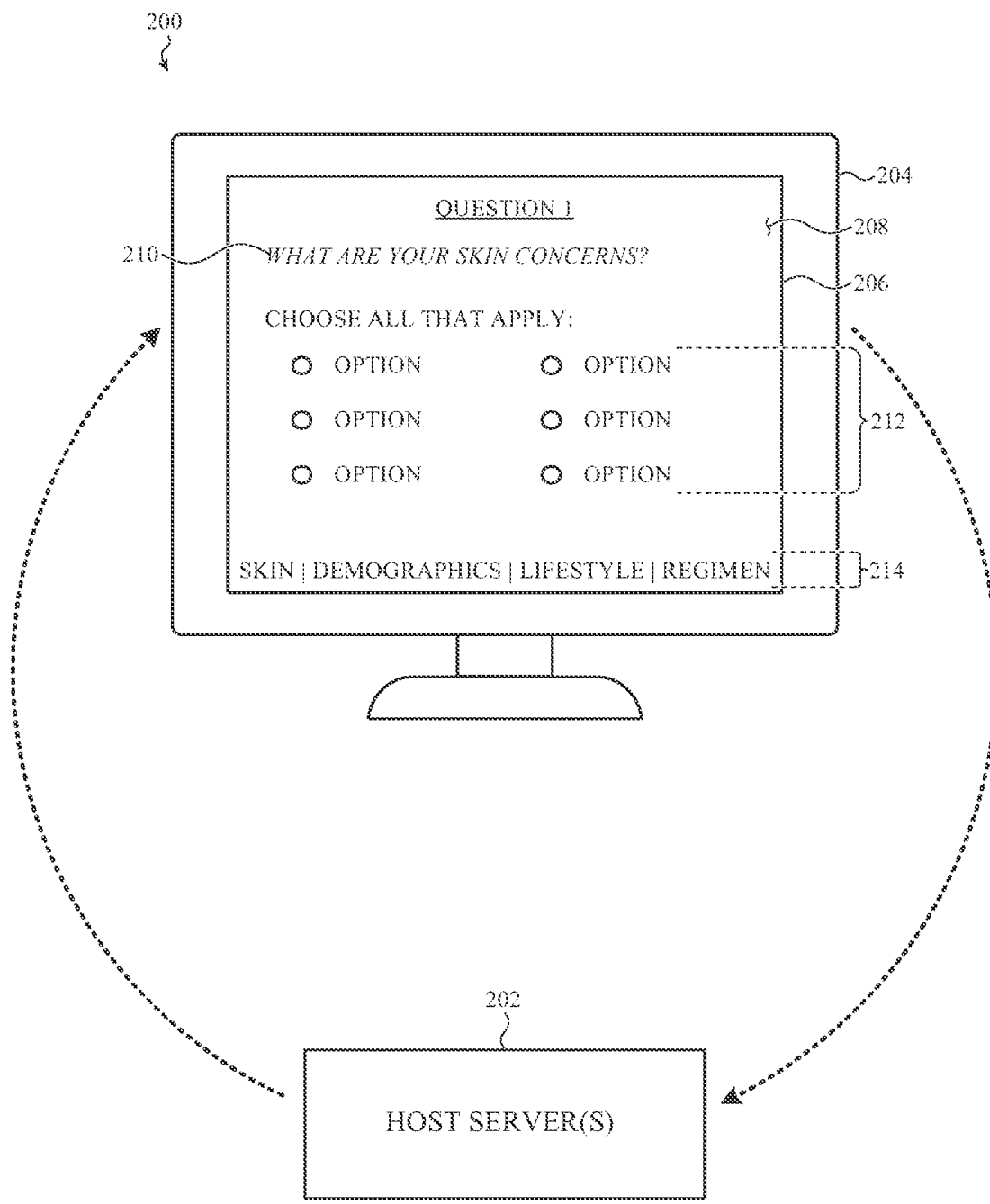
FIG. 2 illustrates an example of a signal/process flow diagram depicting a client device in communication with a skincare system.

FIG. 2 is a signal/process flow diagram depicting a client device in communication with the host server of FIG. 1 and rendering a graphical user interface configured to solicit input from a user of the client device so that the host server can provide a recommendation to that user. In particular, in this embodiment, the recommendation engine 200 includes a host service 202, for example, a skincare system, in communication with a client device 204. The client device 204 includes a display 206 that renders a graphical user interface 208. In this example, the graphical user interface 208 renders a portion of a questionnaire that can be served to the client device 204 to solicit user information from a user operating the client device 204. In this embodiment, the graphical user interface 208 can present a question 210 to the user. In response to the question 210, the user may select one or more options, such as the options 212 to provide demographic information to the host service 202 such that the host service 202 can provide a recommendation for a skincare product to the user. The question(s) asked of the user by the host service 202 can thematically vary (see, e.g., the questionnaire sections 214). For example, as depicted in FIG. 2, questions can be asked of the user related to the user's skin concern and/or concerns, user demographics, user lifestyle (e.g., activity level, outdoor activity, swimming activity, and so on), user skincare regimen, and so on.

Figure 3:
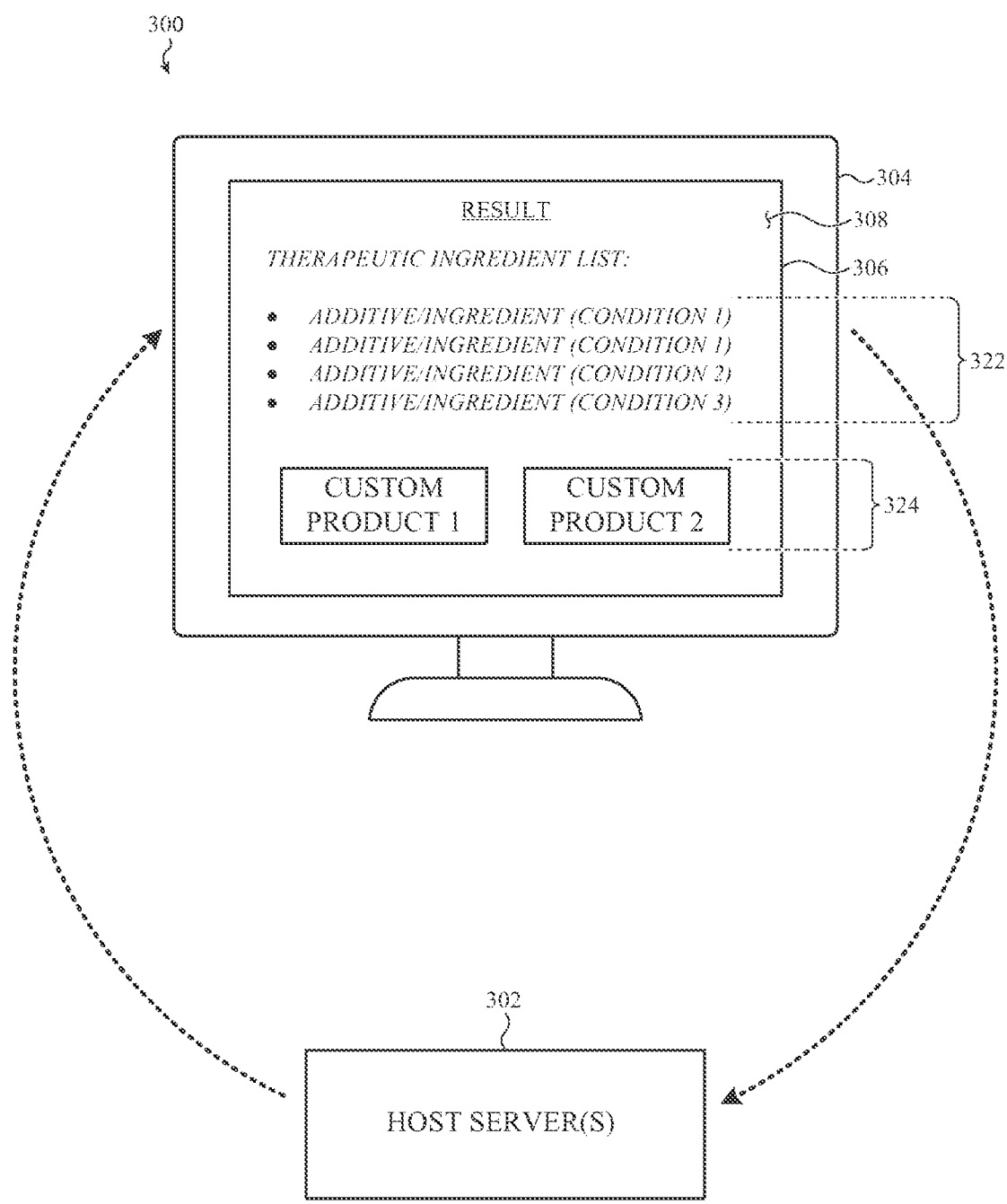
FIG. 3 illustrates an example of a signal/process flow diagram depicting a client device in communication with a skincare system.

The recommendation engine 300 of FIG. 3 can be configured to provide one or more recommendations to the user. FIG. 3 is a signal/process flow diagram depicting the client device of FIG. 1 rendering a graphical user interface presenting one or more product recommendations to the user of the client device. In this embodiment, the host server 302 instructs the client device 304 to display, via the display 306 and the graphical user interface 308, a set of recommendations 322 for the user. In some embodiments, the user may be further presented with an option to purchase a customized product by selecting a custom product 324.

Figure 4:
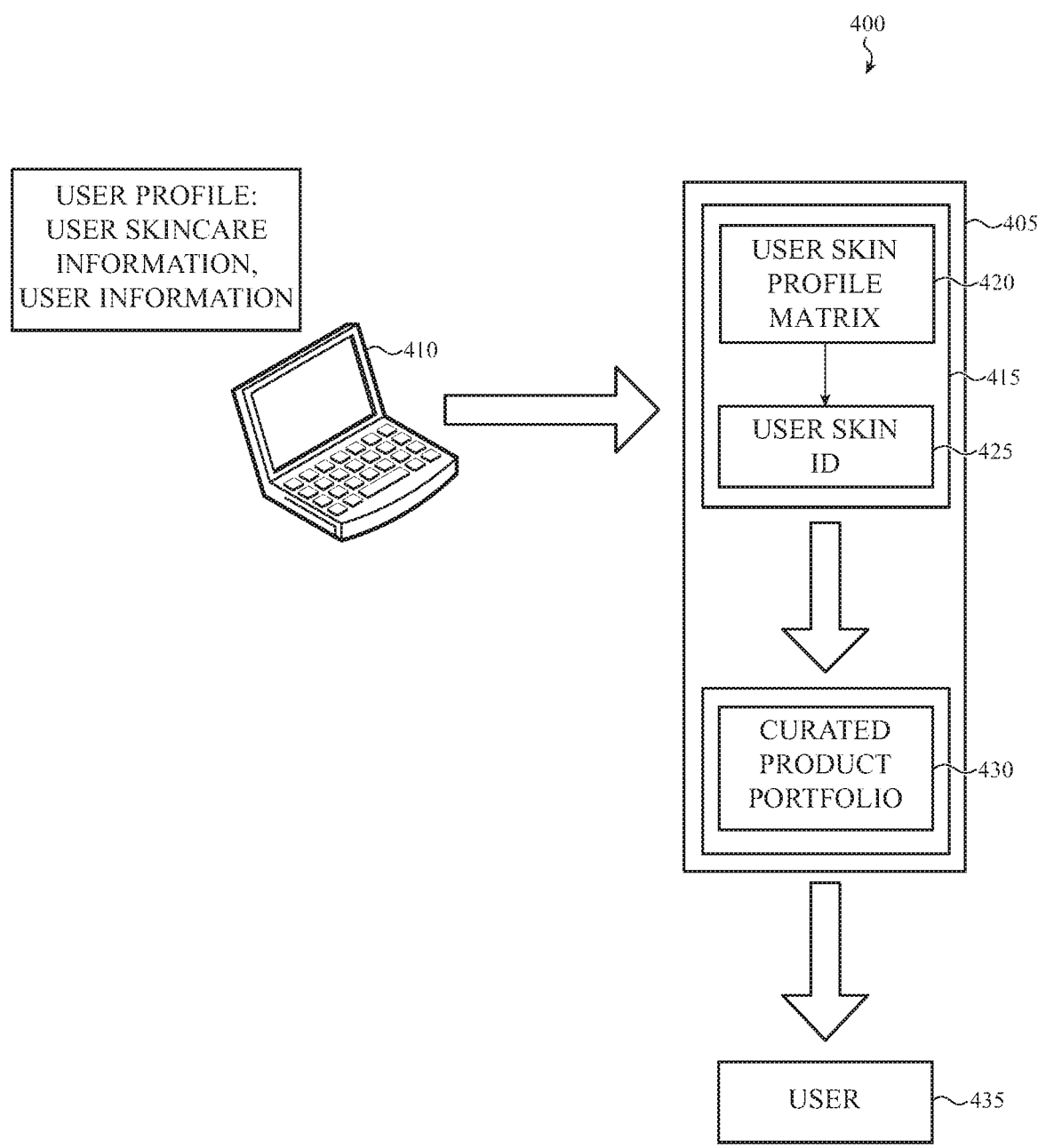
FIG. 4 illustrates an example of a skincare recommendation data flow process.

FIG. 4 illustrates an example of a skincare recommendation data flow process 400, which may include a skincare system 405. In some examples, the skincare system 405 may be configured to receive, process, output, and transmit various types of data which may be skincare related or non-skincare related. In the example of FIG. 4, the skincare system 405 may facilitate receiving user data by a processing block of the skincare system 405. The processing block 415 of the skincare system 405 may receive the user data and may prepare a curated product portfolio 430 which may be provided to a user. In some examples, the processing block may be a processor with a database service configured to translate, correlate, and/or select data in the skincare system 405. The skincare system 405 may or may not include an input device such as a laptop, desktop, mobile device, smart phone, tablet, and so forth. The term input device may be used interchangeably with client device. Additionally, the user skin profile processing performed by the skincare system 405 may occur at the same or different location as the skincare data input by the user.

Generally and as illustrated in FIG. 4, the skincare recommendation data flow process 400 may include an input device 410. The input device 410 may be configured to provide the user with a dynamic questionnaire, for example, via an application or a website. The user skincare data entered at the input device 410 may be provided to the skincare system 405. The skincare system 405 may be provide, via the processing block 415, a user skin profile (not illustrated in FIG. 4) which may be documented by employing a user skin profile matrix 420. The skin profile matrix 420, via the processing block 415, may then be translated into a user skin profile identifier 425, which may be a string of characters, where the characters may be representative of different user skin profile factors. The processing block 415 may include a user skin profile matrix 420 which may be used in conjunction with the user skincare data to generate a user skin identifier 425. The user skin profile identifier 425 may then be used, via the processing block 415, to select a curated product portfolio 430 for the user 435. In some examples, the processing block 415 may operate in the environment of the host server as discussed with reference to FIGS. 4-9.

In FIG. 4, the input device 410 may be employed by the user to enter the user skincare data. The input device 410 may be any appropriate computing device such as a laptop computer, a desktop computer, any type of mobile device, a smart phone, a tablet, and so forth. The user may enter the user skincare data on the input device 410 via a website, application, or any other appropriate data entry system and the user skincare data may be entered on the input device 410 which may be located in retail stores, via any type of personal computing and/or mobile device, or at a facility associated with the product vendor. Although the input device 410 is depicted in FIG. 4 in a different location than the user, the illustration in FIG. 4 is for discussion purposes. In some examples, the user may be in the same location as the input device 410.

The user may input information which may include skin factors and/or non-skin factors. Skin factors may include skin issues and/or skin concerns which may be indicated by the user when entering the user skincare data. Skin issues and skin concerns may include, for example, oil production of the user's skin, allergies to ingredients, specific skin issues such as rosacea, acne, eczema, hyperpigmentation, fine lines, dark circles under the eyes, premature wrinkles, puffy eyes, crerpey skin, any combination thereof, and so forth. Non-skin factors may include user traits that may not be identified by the user as skin concerns. In some examples, non-skin factors may include information regarding the geographic region that the user resides, water intake, activity level, sun exposure, pollution levels, water hardness, activity level, hydration level, gender, hours spent using electronic devices, stress level, hours of sleep, any combination thereof, and so forth. The non-skin related information may still affect a user's skin, but may be general information of the user such as location, hours of sleep, hours of activity, and so forth. The skin factors and non-skin factors are listed as possible examples of the type of data the user may enter, but may include any appropriate data that is skin-related or non-skin related. Non-skin factors may include known dynamic factors or anticipated changes, such as seasonal and temperature changes which may affect the ingredients of the curated product portfolio. These anticipated changes and how they affect the ingredients of the products will be discussed in further detail in at least FIGS. 2 and 3. Though the data to be entered is discussed herein as a list of factors, the data to be entered may be dynamically selected based on the user responses as will be discussed in further detail herein in FIGS. 4-9.

In some examples of FIG. 4, the input device may provide the dynamic questionnaire to the user and the dynamic questionnaire may ask the user questions in an order and with content specific to the user answering those questions. The dynamic questionnaire may be configured to present follow-up questions, to omit irrelevant questions (as determined by user input, user demographics, and/or answers to previously-presented questions), to ask supplemental questions, and so on. The user input of the dynamic questionnaire may provide the skincare system 405 with the user skincare data.

After the user skincare data is entered by a user on the input device 410, the user skincare data may be transmitted to the skincare system 405. The skincare system 405 may receive the user skincare data which may include user skincare information and general user information that may or may not include specific skin information. The user skincare data received by the skincare system 405 may be used to generate a user skin profile. The user skin profile may be an entry in a skincare system 405 database or in some examples may be an entry in a client or customer database. In some examples, a diagnosis of one or more skin concerns presented by the user may be determined by leveraging a predictive model trained by information obtained from at least customer review data scraped from a public resource, a user-specific ingredient list may be determined by leveraging a predictive model trained by information obtained from at least customer review data scraped from a public resource. The user skin profile may be documented in the form of a user skin profile matrix. The user skin profile matrix may be a multidimensional matrix, in that different data points of the user's skin profile may indicate an intersection or correlation of two, three, or more skincare factors. The user skin profile matrix will be discussed in further detail in at least FIGS. 4-6.

The skincare system 405 may be a platform that supports real time or near real time processing of using the skin profile identifier 425 to select the ingredients for the products of the curated product portfolio. The skin profile identifier may be a concatenated string of characters, each of which may represent different user skin care factors from the user skin profile matrix 420. Individual factors of the user skin profile matrix may be assigned to a representative character to create or derive the skin profile identifier 425. The skin profile identifier may include information to create and/or select the curated product portfolio 430. Additionally, in some examples, a user-specific ingredient list may be determined by leveraging a predictive model trained by information obtained from at least customer review data scraped from a public resource. The curated product portfolio 430 may be one or more skincare products, such as, a facial cleanser; a topical sunscreen; a topical serum; an exfoliator; a moisturizer; a chemical peel; a toner; an eye cream; a night cream; or any combination thereof, and so forth. Each of these products of the curated product portfolio may have individually selected ingredients based specifically on the user skin profile.

The curated product portfolio 430 may be provided as a recommendation to the user 435 and the user 435 may review the recommended curated product portfolio 430 soon after entering the user skincare data on the input device 410. In some examples, the recommended curated product portfolio 430 may be provided to the user in real-time, after the user enters the user skincare data. The user 430 may review each product of the curated product portfolio 430 and may review the ingredients of each product. In addition to each of the individual products of the curated product portfolio, a corresponding list of skin issues and/or concerns may be provided for each product and the corresponding list of skin issues may be generated from the initial user profile. Each of the lists that correspond to a product of the curated product portfolio may inform the user which of the concerns are addressed by the individually formulated product. The curated product portfolio and individually formulated products will be discussed in further detail herein with respect to at least FIGS. 4-6.

The curated product portfolio 430 may be recommended to the user 435 via the input device 410 or any other computing device from which the user 430 may access the curated product portfolio 430 and the user 435 may review the individual products, the curated product portfolio 430, the ingredients in each of the individually formulated products, and the skin concerns and/or issues that each product may address. The skincare system 405 may be capable of approximately real-time rendering and the product portfolio recommendations and/or results may be accessible by the user after the user enters the user skin data.

The curated product portfolio or the individual products of the curated product portfolio may be provided to the user 430 for purchase. The user 430 may choose to wait on the purchasing decision, may purchase individual products or may purchase the curated product portfolio 430. In some examples, the skincare system 405 may include a facility to manufacture the individualized products. In other examples, the individualized products may not be manufactured by a facility that is part of the skincare system 405.

The skincare system 405 may provide a recommended curated product portfolio to the user 435. Although in FIG. 4, the user 435 may be depicted at a different location than the input device 410, the user may receive the individualized recommendation at the input device 410 in real-time after entering the requested user skincare data. In some examples, the user 435 may access the recommended curated product portfolio at a later time and/or on a different device, as the user 435 may review the curated product portfolio from any computing device and/or mobile device.

The skincare system 405 may provide the individual products or the entire curated product portfolio to the user 435 for purchase and/or automatic reorder. Additionally, the user 435 may opt to purchase the product or products immediately or in the future. In some examples, the automatic reorder may provide an automatically updated product portfolio which will be discussed in further detail herein. In some examples, the curated product portfolio 430 may be one or more products, and in one example the curated product portfolio 430 may be three separate products. In some examples, the three separate products of the curated product portfolio 430 may be a cleanser, a sunscreen day cream, and a night cream.

Figure 5:
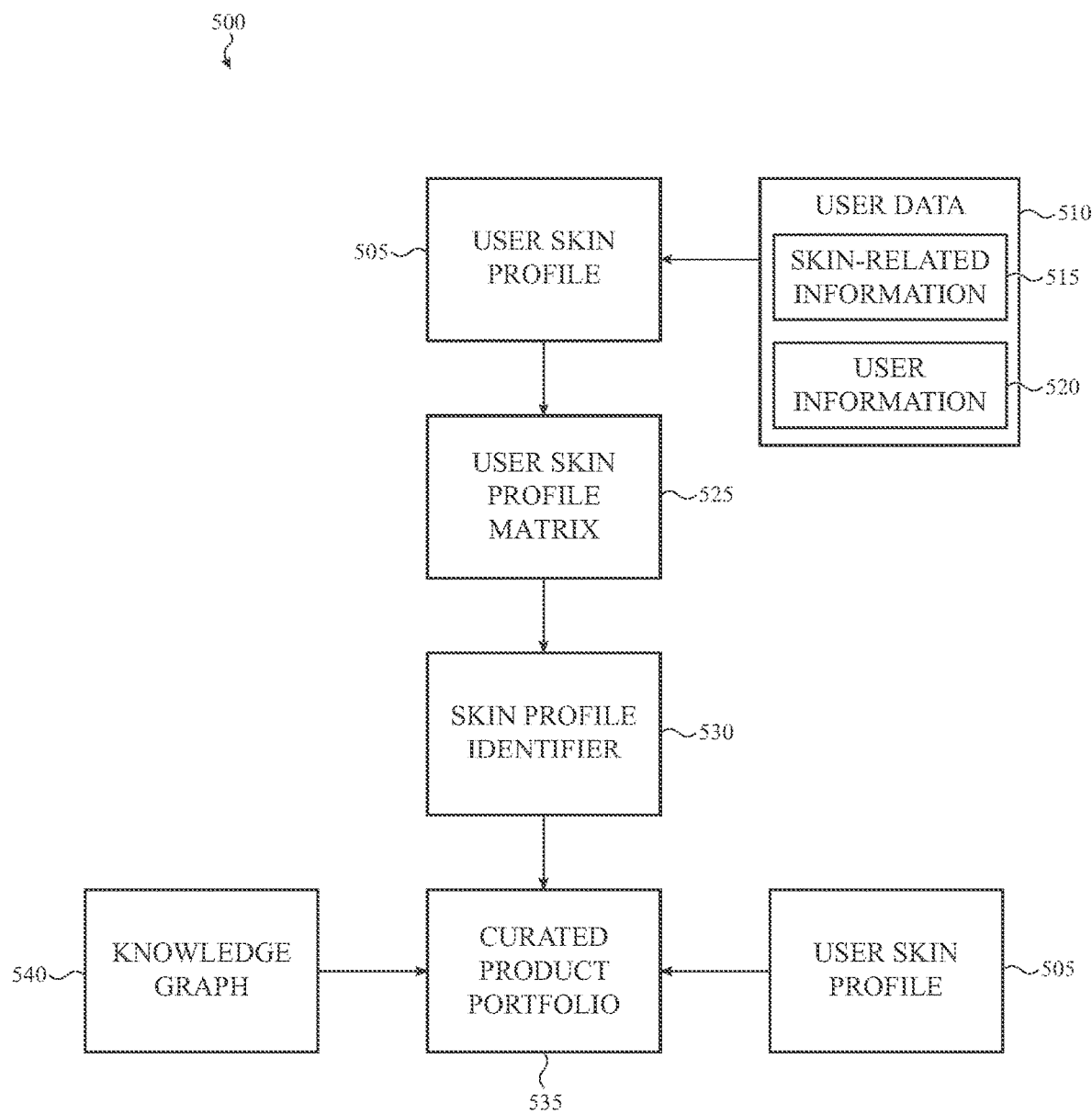
FIG. 5 illustrates an example of a personalization platform for providing a skincare product recommendation.

FIG. 5 illustrates an example of a personalization platform 500 of providing a skincare product recommendation. In the example of FIG. 5, the personalization platform 500 may include receiving user skincare data which may be skincare related data or non-skincare related data and generating a user skincare profile. The user skincare profile may be used to select, prepare, and provide a curated product portfolio to the user. The personalization platform 500 may or may not include an input device such as a laptop, desktop, mobile device, smart phone, tablet, and so forth. Additionally, the processing which may be performed by the personalization platform 500 may occur at the same or different location as the skincare data input by the user.

As illustrated in FIG. 5, the user skin profile 505 may be generated from received user data 510 which may include user skin information 515 and user information 520. The user data 510 may be the raw data which is entered by the user as discussed with respect to FIG. 1. In some examples, the user skin profile 505 may be included in a skincare database, which may include appropriate data formatting and database identifiers. In some examples, a diagnosis of one or more skin concerns presented by the user may be determined by leveraging a predictive model trained by information obtained from at least customer review data scraped from a public resource. The diagnosis determined by the predictive model may also be included in the user skin profile 505. The user skin profile 505 may be documented in a user skin profile matrix 510.

User skin profile matrix 510 may organize the user data 510, which may include two types of information, a first type which may be user skin-related information 515 and user information 520. The skin-related information 515 may include skin issues and/or skin concerns identified by the user. The user information may include information that is non-skin related information such as general information regarding the user and the user's lifestyle. The user information may include at least: the location of the user; water intake; activity level; sun exposure; pollution levels; water hardness; activity level; hydration level; gender; hours spent using electronic devices; stress level; hours of sleep; ethnicity; or any combination thereof; and so forth. The skin factors and non-skin factors are listed as possible examples of the type of data the user may enter, and may include any additional appropriate data that is skin-related or non-skin related.

User skin profile matrix 525 may include skin matrix factors which may be organized into two or more dimensions. In some examples, there may be a greater number of skin matrix factors than user data factors. For example, user data 510 may include the user's geographic location, but the skin matrix factors may include various types of information about the user's geographic location. For example, pollution levels, water hardness, UV exposure, humidity, temperature, allergen information for native grasses, trees, molds, flowers, and so forth, may all be skin matrix factors that correspond to the user's geographic location. User skin profile matrix 525 may automatically account for the additional corresponding data for skin matrix factors which may be associated with the user data 510.

The skin matrix factors of the user skin profile matrix may have individual representative markers associated with and corresponding to each skin matrix factor. In one example, a skin matrix factor may have varying degrees and each of these varying degrees of the skin matrix factor may have an associated individual representative marker. For example, UV exposure may have five different representative markers associated with it which may correspond to five different levels of UV exposure. In some examples, very low UV exposure may have a first representative marker, low UV exposure may have a second representative marker, average UV exposure may have a third representative marker, high UV exposure may have a fourth representative marker, and very high UV exposure may have a fifth representative marker. These representative markers may be used in the skin user identifier discussed herein and at least in the discussion of FIG. 5.

Additionally, in some examples, the user skin profile matrix may be a multidimensional matrix, in that different data points of the user's skin profile may indicate an intersection or correlation of two, three, or more skincare factors. For example, a user's skin profile may include the correlated or intersecting skincare factors of being 19 years old, having oily skin, and living in a high humidity climate. Although each of these factors may be accounted for individually in multiple skincare products, when the intersecting skincare factors are simultaneously accounted for, a more effective skincare recommendation and product or product line may be provided to the user.

The user skin profile 505 may be documented in the user skin profile matrix 525 at the level of the skin matrix factors and the corresponding individual representative markers. After the user data 510 is received and the user skin profile 505 is generated, the individual elements or factors of the user skin profile 505 may be mapped to the skin matrix factors to produce the user skin profile matrix 525. In some examples, each individual element or trait of the user skin profile 505 may be matched or mapped to the appropriate corresponding skin matrix factor(s) in the user skin profile matrix 525. For example, a user skin profile 505 may include a user location in New Orleans which may correspond to a number of skin matrix factors including, among other factors, humidity levels. The user skin profile 505 user location, may map to a corresponding skin matrix factor of a very high level of humidity. Further, there may be an individual representative marker which may correspond to the skin matrix factor of a very high level of humidity.

The skin matrix factors and accordingly, the user skin profile matrix 525 may be dynamic and may change according to any relevant information. For example, in the future, a skin matrix factor may change such as the season or temperature. Because this change alters the skin matrix factor, the user skin profile matrix 525 changes as well. Additionally, this changing factor may interact with other skin matrix factors, thus further altering the user skin profile matrix 525.

The skin profile identifier 530 may be derived from the user skin profile matrix 525. As previously discussed, the user skin profile matrix 525 may have individual representative markers for each of the skin matrix factors. In some examples, the skin profile identifier 530 may be a concatenated string of individual representative markers from the user skin profile matrix 525. Although the skin profile identifier may be any number of characters, in some examples, the skin profile identifier 530 may be 58 characters long and these characters may be used to select the ingredients in the products. The selection of the ingredients may additionally be based on the highest likelihood of achieving the best results for the user. Furthermore, in some examples, a user-specific ingredient list may be determined by leveraging a predictive model trained by information obtained from at least customer review data scraped from a public resource. As such, in some examples, the curated ingredient list may be determined using both the predictive model and the skin profile identifier 530.

In some examples, the skin profile identifier 530 may differ from the user skin profile 505 and the user data 510. As previously discussed, the user data 510 may be the raw data entered by the user and the user skin profile 505 may be generated by the skincare system which may include a database service and the user skin profile 505 may be an entry in a user database. The skin profile identifier 530 may include a string of characters which correspond to individual representative markers. The individual representative markers may be unique identifiers that correspond to skin matrix factors included in the user skin profile matrix 525. In some examples, the characters of the skin profile identifier may be either representative of a skin-related factor such as dry skin or a non-skin related factor such as the humidity level. The skin profile identifier 530 may, at a high level, be used to map the user skin profile 505 to base ingredients and additives for formulating the product portfolio for the user. By using this personalization skincare platform, the products of the product portfolio are individualized and curated products for the user.

In some examples, the skin profile identifier 530 may be updated or may change according to anticipated changes to the user skin profile 505. The skincare system may include the dynamic and automated ability to generate an updated user skin profile based on existing user data which may be dynamic, for example seasons associated with a user's location. The user skin profile and the user skin profile matrix may be automatically updated when existing user data includes anticipated changes in the user information. Accordingly, the skin profile identifier 530 may be updated based on the anticipated change associated with the user skin profile. In some examples, the user skin profile 505 may not change and the skin profile identifier may be updated based on a trigger which will be discussed in further detail herein. Because the skin profile identifier 530 may be updated, the curated product portfolio 535 may also be altered and the updated products may be recommended to the user, provided to the user for purchase, or automatically sent to the user.

Anticipated changes may be built into the skin profile identifier and may be triggered or signaled by various factors. In this example, there may not be a change or update to the user skin profile 505 even though the skin profile identifier 530 may be updated. In some examples, the anticipated change to the skin profile identifier may be triggered by the time of year which may indicate a change in season and accordingly a temperature change depending on the geographic location of the user. For example, the user data 510 and the user skin profile 505 may indicate that the user location is in Minnesota where the seasons change and there are significant variations in the temperature. As the temperature changes, the skin profile identifier 530 may be updated which may affect the selection of the product ingredients. The curated product portfolio 535 may be updated based on the anticipated change or changes.

The curated product portfolio 535 may be selected based at least partially on the skin profile identifier 530 and the knowledge graph 545. The knowledge graph 545 may include information regarding the effectiveness of the base ingredients and additives which may be selected to formulate the curated product portfolio 535, as well as interactions between the base ingredients and additives. The products may include one or more base ingredients and one or more additives. The base ingredient may be a relatively benign carrier base or foundation into which the active ingredients or additives may be added.

The knowledge graph 545 may effectively and accurately match the skin profile identifier to the appropriate ingredients that may address the user's skin issues and may provide the highest likelihood of success by addressing and/or improving the user's skin issues. Using the knowledge graph 545 and the skin profile identifier 530, base ingredients and additives may be selected for each of the products of the curated product portfolio 535. Selecting the base ingredients and additives based on the skin profile identifier and knowledge graph may provide a highly individualized and specific product portfolio to the client since there are at least hundreds of thousands of available combinations.

Further, in some examples, one or more additives may be selected and combined together, and even though the additives may interact with one another, this interaction may be accounted for when formulating the curated product portfolio. In some examples, combining certain base ingredient and additive combinations may be more or less effective for different factors such as varying levels of humidity or gender and the efficacy of the combinations in different environmental conditions and other varying conditions may be accounted for and addressed while selecting ingredients.

Each product of the curated product portfolio 535 may have one or more lists associated with each of the products. In some examples, the active ingredients may be listed and if desired the full ingredient list, including relatively benign ingredients, may also be accessed and reviewed by the user. In some examples, each of the products may include a list of concerns which the product may address. The concerns may correspond to skin issues or concerns that the user indicated when entering the initial user data 510.

In some examples, the curated product portfolio 535 may include three products. Each product may address a different skin issue or two or more products may address the same skin issue indicated by the user. Each product may include different ingredients than the other products, but even though the ingredients may be different product to product, each product may include complementary ingredients to the ingredients of the other products. The products may available for individual purchase by the client or may be available for purchase as a curated product portfolio or product set. In some examples, the clients may automatically receive the curated product set after a predetermined time interval, such as every two months.

FIG. 6 illustrates an example skincare matrix 600. In some examples, the matrix 600 depicted in FIG. 6 may be configured to logically provide a mapping to a user skin profile. In the example of FIG. 6, the matrix 600 may include at least multiple rows and columns of skin matrix factors. The matrix may be used to correlate the user skin profile to the skin matrix factors and the matrix may be used to generate a skin profile identifier which may be used to select, prepare, and provide a curated product portfolio to the user.

By way of example and for purposes of description, the matrix 600 may be a set number of rows and columns of skin matrix factors for discussion purposes only, and in practice may be any appropriate number of rows and columns. The skin matrix factors of FIG. 6 are organized in the matrix 600 and may be similar to the skin matrix factors as discussed with reference to FIGS. 4 and 5. The matrix 600 may be used for to generate a skin profile identifier.

As illustrated in FIG. 6, the matrix 600 may include rows and columns of various skin matrix factors. The skin matrix factors may include any relevant factor that may affect the skin and/or skin concerns of the user. In some examples of FIG. 6, the columns may be different skin matrix factors and may include skin-related information and non-skin related information. As previously discussed, the non-skin related information may still affect a user's skin, but may be general information of the user such as location, hours of sleep, hours of activity, and so forth. The columns may include factors such as hyperpigmentation, fine lines, and eczema, and may also include other factors such as ethnicity, gender, age, UV exposure, and water hardness. In some examples of FIG. 6, the rows may be varying degrees of the skin matrix factors listed in the columns. For example, matrix factor x1 may be UV exposure and matrix factors y1 through y5 may be the degree of UV exposure. In some examples, matrix factor y1 may be very low UV exposure, matrix factor y2 may be low UV exposure, matrix y3 may be average UV exposure, matrix factor y4 may be high UV exposure, and matrix factor y5 may be very high UV exposure.

Although each column may be different, the rows may still be varying degrees of the column skin matrix factors. For example, the column may be humidity and the rows may be varying degrees of very low to very high which may correlate to the column humidity. In still further examples, the column may be sensitive skin and the rows may include varying degrees of the skin sensitivity of the user or vice versa. In some examples, the rows and columns may both include skin matrix factors including skin-related factors and non-skin related factors.

In FIG. 6, the user skin profile matrix 600 includes examples of alpha numeric individual representative markers A11, B22, C35, and D43. These individual representative marks are provided for discussion purposes only and may be any type of identifier that is representative of the user's skin information and general information. An individual representative marker may be one character or multiple characters as appropriate. In FIG. 6, the individual representative marker may provide information of the skin matrix factor x1 which may be sensitive skin. Because the individual representative marker is A11, this may indicate that the user has sensitive skin, but that the sensitive skin is low level, which is indicated by the second one. In the example, the user does not have sensitive skin, the individual representative marker may be A00 which may indicate that A represents sensitive skin, but the zeros indicate that the user does not have sensitive skin. The individual representative marker C35 may indicate that the user lives in a very high level humidity area, where the skin matrix factor x3 may be humidity level. In this example, the individual representative markers may be concatenated to form the skin profile identifier. Additionally, in this example, the skin profile identifier may have four concatenated individual representative markers, but may be any appropriate number of concatenated markers.

The matrix 600 may be a multidimensional matrix beyond being a two dimensional, rows and columns, matrix. The matrix 600 may be a multidimensional matrix, in that different data points of the user's skin profile may indicate an intersection or correlation of two, three, or more skincare factors. For example, a user's skin profile may include the correlated or intersecting skincare factors of being 19 years old, having oily skin, and living in a high humidity climate. Although each of these factors may be accounted for individually in multiple skincare products, when the intersecting skincare factors are simultaneously accounted for, a more effective skincare recommendation and product or product line may be provided to the user.

In some examples, the skin matrix factors may interact with one another. For example, if a first user has dry skin and lives in a location with high UV exposure and a second user has oily skin and lives in the same location with high UV exposure, the matrix 600 may account for the intersection of these factors in another dimension of the matrix that is not illustrated in FIG. 6.

Figure 7:
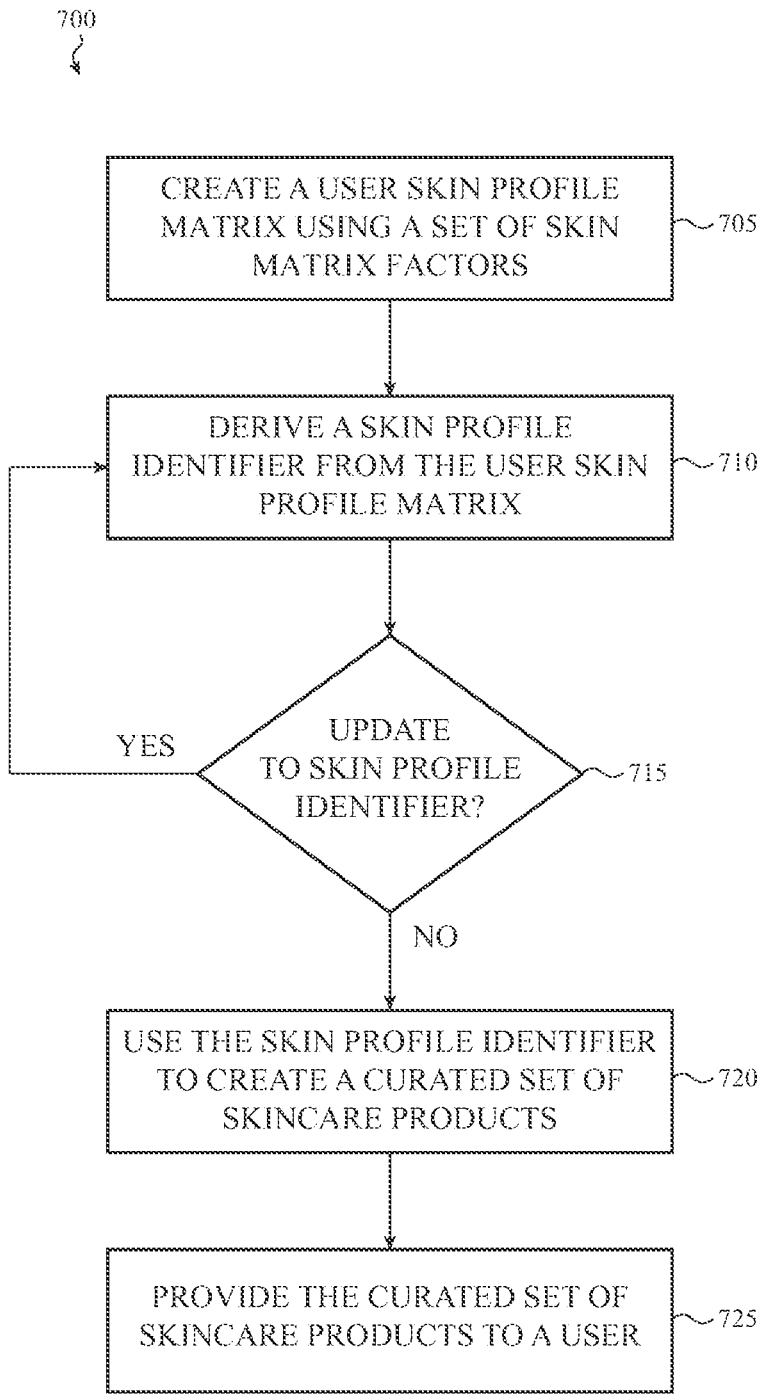
FIG. 7 illustrates an example method for providing a skincare product recommendation.

FIG. 7 illustrates an example method 700 for providing a skincare product recommendation. In some examples, the method 700 depicted in FIG. 7 may include additional processes not depicted in FIG. 7, or may exclude some of the processes in FIG. 7. Further, the processes of FIG. 7 are ordered for purposes of discussion, but may, in some examples, be performed in a different order. In the example of FIG. 7, the method 700 may include processes to correlate a user skin profile to the skin matrix factors to generate a skin profile identifier. The skin profile identifier may be used to select, prepare, and provide a curated product portfolio to the user.

In FIG. 7 and at 705 a user skin profile matrix may be created using a set of skin matrix factors. The user skin profile matrix may organize the user data, which may include skin matrix factors. The skin matrix factors may include skin-related factors and non-skin related factors. The skin-related factors may include skin concerns, skin type, allergies, skin issues, and so forth, while the non-skin related factors may be general information on the user. The non-skin related factors may include where the user lives, ethnicity, age, water intake, stress level, and so forth. The user skin profile matrix may include the skin matrix factors which may affect the skin of a user or which may exacerbate any existing skin conditions of the user.

At 710, a skin profile identifier may be derived from the user skin profile matrix. The skin profile identifier may be derived from mapping the user skin profile to the skin matrix factors of the user skin profile matrix. In some examples, the skin profile identifier may be a concatenated string of individual representative markers from the user skin profile matrix. The individual representative markers may represent unique intersections of the skin matrix factors.

At 715, updates to the skin profile identifier are verified. In some examples, the skin profile identifier includes an anticipated change. As discussed herein, the skin profile identifier may be updated based on the anticipated change associated with the user skin profile. In some examples, the user skin profile may not change and the skin profile identifier may be updated based on a trigger such as the month of the year. Because the skin profile identifier may be updated, the curated product portfolio may also be altered and the updated products may be recommended to the user or provided to the user for purchase.

Anticipated changes may be built into the skin profile identifier and may be triggered or signaled by various factors. In this example, there may not be a change or update to the user skin profile even though the skin profile identifier may be updated. In some examples, the anticipated change to the skin profile identifier may be triggered by the time of year which may indicate a change in season and accordingly a temperature change depending on the geographic location of the user. The curated product portfolio may be updated based on the anticipated change or changes.

As indicated at 715, if it is confirmed that there are no updates to the skin profile identifier, then at 720, the skin profile identifier may be used to create a curated set of skincare products. The skin profile identifier may be used to select the appropriate and effective base ingredient and additives to address the skin issues and concerns of the user. At 725, the curated set of skincare products may be provided to the user for review and/or purchase.

Figure 8:
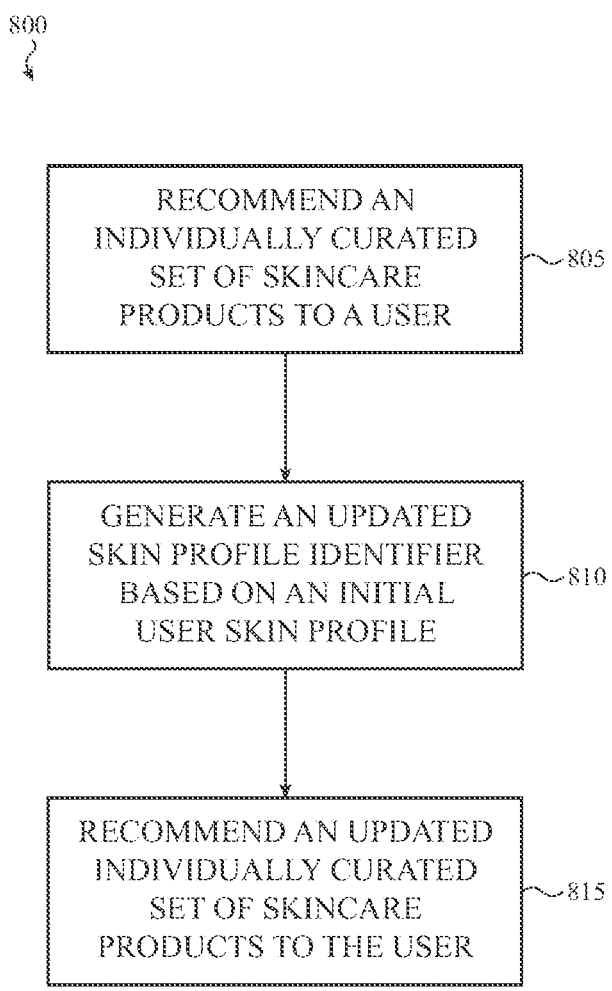
FIG. 8 illustrates an example method for providing and updating a skincare product recommendation.

FIG. 8 illustrates an example method 800 for providing and updating a skincare product recommendation. In some examples, the method 800 depicted in FIG. 8 may include additional processes not depicted in FIG. 8, or may exclude some of the processes included in FIG. 8. Further, the processes of FIG. 8 are ordered for purposes of discussion, but may, in some examples, be performed in a different order. In the example of FIG. 8, the method 800 may include processes to correlate a user skin profile to the skin matrix factors to generate a skin profile identifier. The skin profile identifier may be used to select, prepare, and provide a curated product portfolio to the user.

In FIG. 8 and at 805, an individually curated set of skincare products may be recommended to the user. The set of skincare products may be specifically formulated according to the initial skincare data entered by the user. The initial skincare data may be received by the skincare system and entered into the database and a user skincare profile may be created. The user skincare profile may be mapped to the skin matrix factors of the user skin profile matrix to derive a skin profile identifier. In some examples, the individual elements of the user skincare profile may be matched to the corresponding skin matrix factors of the user skin profile matrix to derive a skin profile identifier. The user skin profile matrix may include skin matrix factors as discussed herein with respect to at least FIGS. 4-6. Each of the skin matrix factors may have an individual representative marker and these markers may be concatenated together to make up the skin profile identifier.

In some examples, the initial skincare data and the skin profile identifier may include an anticipated change due to temperature or humidity changes for example. As discussed herein and at 810, an updated skin profile identifier may be generated based on the anticipated change associated with the initial user skin profile. In some examples, the user skin profile may not change and the skin profile identifier may be updated based on a trigger as discussed herein. Because the skin profile identifier may be updated, the curated product portfolio may also be altered and the updated products may be recommended to the user or provided to the user for purchase as indicated at 815.

Figure 9:
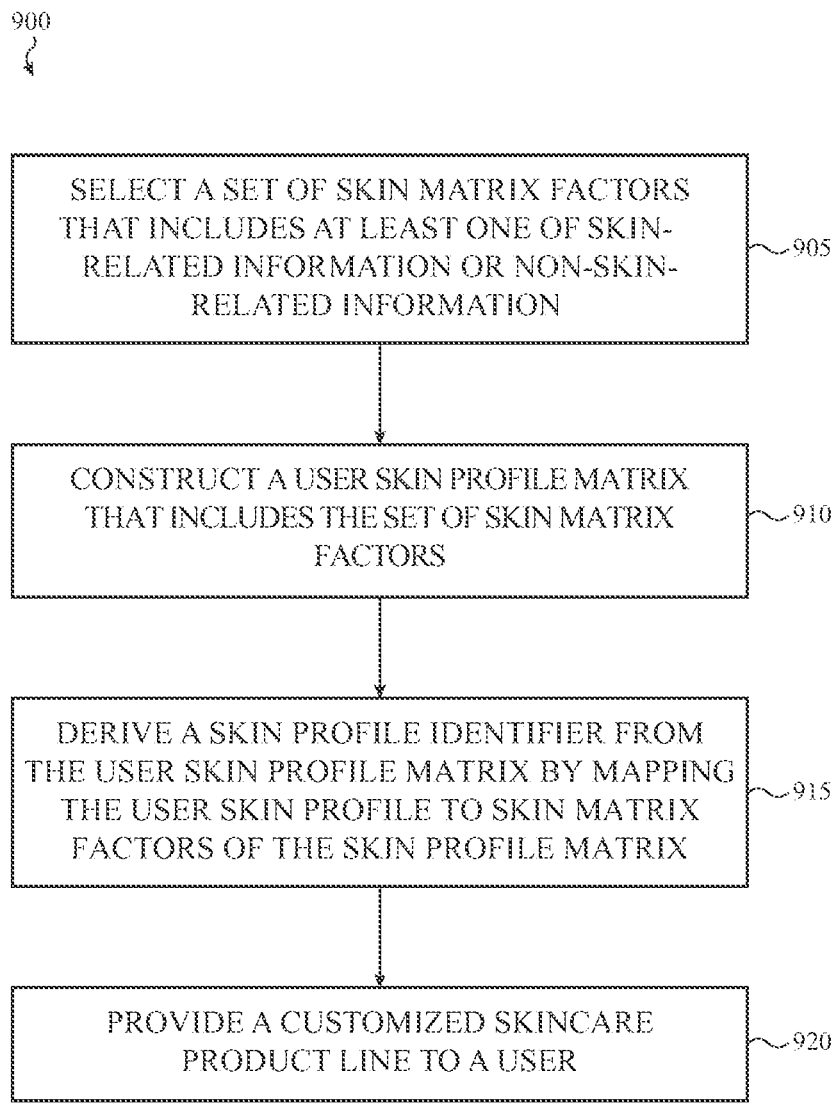
FIG. 9 illustrates an example method for providing a skincare product recommendation.

FIG. 9 illustrates an example method 900 for providing a skincare product recommendation. In some examples, the method 900 depicted in FIG. 9 may include additional processes not depicted in FIG. 9, or may exclude some of the processes included in FIG. 9. Further, the processes of FIG. 9 are ordered for purposes of discussion, but may, in some examples, be performed in a different order. In the example of FIG. 9, the method 900 may include processes to correlate a user skin profile to the skin matrix factors to generate a skin profile identifier. The skin profile identifier may be used to select, prepare, and provide a curated product portfolio to the user.

In FIG. 9 and at 905, a set of skin matrix factors that includes at least one of a skin-related information or non-skin related information may be selected. The skin matrix factors may be selected based on whether the factor may affect a user's skin. These factors may include skin-related factors and non-skin related factors such as general user information.

At 910, a user skin profile matrix may be constructed that includes the set of skin matrix factors and at 915, a skin profile identifier may be derived from the user skin profile matrix by mapping the user skin profile to skin matrix factors of the user skin profile matrix. The user skin profile matrix may include intersections of various skin matrix factors. The skin matrix factors may include any relevant factor that may affect the skin and/or skin concerns of the user. In some examples, the skin profile identifier may be a concatenated string of individual representative markers from the user skin profile matrix. The skin profile identifier may then be used to select the base ingredients and the additives appropriate to address the skincare needs of the user and a customized skincare product line may be provided to the user at 920.

The described systems, process flows, and methods of the selection and recommendation of the curated product portfolios in FIG. 1-9 have been for explanatory purposes. In alternative embodiments, the described embodiments may include a different combination or configuration of processes, or may perform additional or alternative functions. The process flows and configurations described herein may be used as part of a skincare system which may recommend a curated product portfolio, or in any other appropriate skincare system.

The foregoing description, for purposes of explanation, uses specific nomenclature to provide a thorough understanding of the described embodiments. However, it will be apparent to one skilled in the art, after reading this description, that the specific details are not required in order to practice the described embodiments. Thus, the foregoing descriptions of the specific embodiments described herein are presented for purposes of illustration and description. They are not targeted to be exhaustive or to limit the embodiments to the precise forms disclosed. It will be apparent to one of ordinary skill in the art, after reading this description, that many modifications and variations are possible in view of the above teachings.

The present disclosure recognizes that personal information data, including the skincare data acquired using the presently described technology, can be used to the benefit of users. In some examples, user skincare data is collected for providing users with feedback about their health or fitness levels, or the effectiveness of ingredients in the products or the products themselves. Further, other uses for personal information data, including skincare data that benefit the user are also contemplated by the present disclosure.

The present disclosure further contemplates that the entities responsible for the collection, analysis, disclosure, transfer, storage, or other use of such personal information data will comply with well-established privacy policies and/or privacy practices. In particular, such entities should implement and consistently use privacy policies and practices that are generally recognized as meeting or exceeding industry or governmental requirements for maintaining personal information data private and secure, including the use of data encryption and security methods that meets or exceeds industry or government standards. For example, personal information from users should be collected for legitimate and reasonable uses of the entity and not shared or sold outside of those legitimate uses. Further, such collection should occur only after receiving the informed consent of the users. Additionally, such entities would take any needed steps for safeguarding and securing access to such personal information data and ensuring that others with access to the personal information data adhere to their privacy policies and procedures. Further, such entities can subject themselves to evaluation by third parties to certify their adherence to widely accepted privacy policies and practices.

Despite the foregoing, the present disclosure also contemplates embodiments in which users selectively block the use of, or access to, personal information data, including skincare data. That is, the present disclosure contemplates that hardware and/or software elements can be provided to prevent or block access to such personal information data. In some examples, users can select to remove, disable, or restrict access to certain health-related applications collecting users' personal health or fitness data, skincare data, or general information on the user.

What is claimed is:

1. A method of operating a host service communicably coupled to a client device operated by a user, the method comprising:
   creating, by the host service, a user skin profile comprising a user skin profile matrix, the user skin profile matrix comprising a set of skin matrix factors based, at least in part, on:
      skin-related information received by the host service in response to a first user input provided by the user to the client device; and
      nonskin-related information received by the host service in response to a second user input provided by the user to the client device;
   modifying, by the host service, the user skin profile matrix of the user skin profile by changing at least one skin matrix factor of the set of skin matrix factors according to an anticipated change in nonskin-related information in an upcoming time period;
   deriving, by the host service, a skin profile identifier from the modified user skin profile matrix;
   generating, by the host service based on the skin profile identifier, a user-specific set of skincare product ingredients;
   selecting, based on the user-specific set of skincare product ingredients, a curated set of products;
   providing the curated set of skincare products to the user;
   transmitting identifying information regarding the curated set of skincare products and a skincare regimen recommendation to the user, the skincare regimen recommendation based at least in part on the curated set of skincare products;
   scheduling at least one automatic update to the curated set of skincare products for the user based at least in part on the user skin profile;
   creating an updated curated set of skincare products for the user when a scheduled automatic update signals an anticipated change to the user skin profile; and
   providing the updated curated set of skincare products to the user.

2. The method of claim 1, wherein deriving the skin profile identifier from the user skin profile matrix comprises mapping the user skin profile to the user skin profile matrix.

3. The method of claim 1, further comprising:
   receiving user data from the client device at the host service, the user comprising the first input and the second input.

4. The method of claim 1, further comprising:
   generating the user skin profile, wherein the user skin profile comprises nonskin-related information based on at least one of seasonal variations or environmental conditions.

5. The method of claim 1, further comprising:
   selecting the set of skin matrix factors to represent the user skin profile, wherein the set of skin matrix factors comprises at least one of demographic information or user skin concern information.

6. The method of claim 1, further comprising:
   assigning an individual representative marker defining a graduated scale of possible values to at least one of the skin matrix factors of the set of skin matrix factors of the user skin profile matrix.

7. The method of claim 1, wherein deriving the skin profile identifier from the user skin profile matrix comprises concatenating individual representative markers of at least two of the skin matrix factors mapped to the user skin profile.

8. A method of dynamically providing a skincare product recommendation to a user operating a client device in communication with a host service, the method comprising:
    determining, by the host service, a user-specific set of skincare product ingredients based at least in part on an initial user skin profile associated with the user;
    scheduling, by the host service, updates to the user skin profile, each update based, at least in part on, a respective anticipated environmental change to nonskin-related information of a prior user skin profile; and
    for each scheduled update to the user skin profile:
        determining, by the host service, an updated user-specific set of skincare product ingredients based on the updated user skin profile;
        selecting at least one curated skincare product comprising the updated user-specific set of skincare product ingredients;
        providing the at least one curated skincare product to the user; and
        transmitting, by the host service to the client device, identifying information associated with the at least one curated skincare product.

9. The method of claim 8, further comprising:
generating an initial skin profile identifier by correlating the initial user skin profile to a user skin profile matrix.

10. The method of claim 9, further comprising:
creating the user skin profile matrix by selecting a set of skin matrix factors that include at least one of a set of skin-related factors or a set of nonskin-related factors.

11. The method of claim 8, wherein selecting the at least one curated skincare product comprises:
    formulating the at least one curated skincare product by:
        selecting, by the host service based on the updated user-specific set of skincare product ingredients, at least one base ingredient from a set of base ingredients; and
        selecting, by the host service based on the updated user-specific set of skincare product ingredients, at least one additive from a set of additives.

12. The method of claim 11, further comprising:
changing, based on the updated skin profile identifier, at least one of:
    at least one selected based ingredient selected from the set of base ingredients; or
    at least one selected additive selected from the set of additives.

13. The method of claim 8, wherein generating the updated skin profile identifier comprises triggering an anticipated update to the initial user skin profile.

14. The method of claim 8, wherein generating the updated user skin profile comprises modifying the initial user skin profile based on an anticipated environmental change that impacts an efficacy of at least one of the user-specific set of skincare product ingredients.

15. A method of automatically generating and updating a user-specific skincare product and skincare regimen for a user, the method comprising:
    selecting, by a host service instance instantiated by a host server in communication with a client device associated with the user, a set of skin matrix factors that includes:
        at least one skin-related data item associated with the user and received by the host service from the client device; and
        at least one nonskin-related data item associated with the user and received by the host service from the client device;
    defining, by the host service, a user skin profile matrix from the set of skin matrix factors;
    defining, by the host service, a skin profile identifier from the user skin profile matrix by mapping individual elements of the user skin profile to the skin matrix factors of the user skin profile matrix;
    selecting, by the host service, a set of skincare product ingredients specific to the skin profile identifier;
    selecting, by the host service, a set of skincare product formulations collectively comprising the selected set of skincare product ingredients;
    communicating to the user, regimen information associated with use of the selected set of skincare product formulations; and
    scheduling, by the host service, updates to the skin profile identifier, each scheduled update to the skin profile identifier based on at least one respective anticipated change to environmental nonskin-related data items of a prior user skin profile wherein, for each scheduled update of the skin profile identifier:
        selecting, by the host service, an updated set of skincare product ingredients specific to the respective updated skin profile identifier;
        selecting, by the host service, an updated set of skincare product formulations collectively comprising the updated selected set of skincare product ingredients;
        providing the updated set of skincare product formulations as an updated set of skincare products to the user; and
    transmitting, by the host service, regimen information associated with use of the updated set of skincare product formulations.

16. The method of claim 15, further comprising:
modifying the updated set of skincare product ingredients in response to a change to the user skin profile received from the client device.

17. The method of claim 15, wherein the selected set of skincare product ingredients comprises at least one base ingredient and at least one additive ingredient, each selected based at least in part on the skin profile identifier.

* * * * *